United States Patent
Miscioscia (12)

(10) Patent No.: US 6,656,485 B1
(45) Date of Patent: Dec. 2, 2003

(54) PRODUCTS FOR BODY HYGIENE BASED ON LAPACHO EXTRACTS CONTAINING QUERCITINE, THEIR PREPARATION AND USE

(75) Inventor: Mario Miscioscia, Turin (IT)

(73) Assignee: Euro-Pharma S.r.l., Turin (IT)

( * ) Notice: Subject to any disclaimer, the term of this patent is extended or adjusted under 35 U.S.C. 154(b) by 0 days.

(21) Appl. No.: 09/830,861

(22) PCT Filed: Oct. 22, 1999

(86) PCT No.: PCT/EP99/08032

§ 371 (c)(1),
(2), (4) Date: Sep. 7, 2001

(87) PCT Pub. No.: WO00/26207

PCT Pub. Date: May 11, 2000

(30) Foreign Application Priority Data

Oct. 30, 1998 (IT) ......................................... FI98A0238

(51) Int. Cl.[7] ............................ A61K 9/68; A61K 7/26; A61K 35/78; A61K 9/20; A01N 65/00
(52) U.S. Cl. ........................... 424/401; 424/48; 424/58; 424/74; 424/440; 424/464; 424/769; 424/775
(58) Field of Search ................................. 424/769, 775, 424/401, 440, 464, 58, 74, 48

(56) References Cited

U.S. PATENT DOCUMENTS

| 3,178,345 A | 4/1965 | Schlagel |
| 3,810,990 A | 5/1974 | Jurd et al. |
| 5,455,033 A | * 10/1995 | Silverman et al. ............ 424/737 |

FOREIGN PATENT DOCUMENTS

| DE | 1 793 025 | 2/1972 |
| DE | 196 00 543 A1 | 7/1996 |
| EP | 0 019 081 A1 | 11/1980 |

OTHER PUBLICATIONS

Computer Caba Abstract 94:53172 Anesini et al "Screening of Plants Used in Argentine Folk Medicine for Antimicrobial Activity" J. Ethnopharm. (1993) VOL 39 NO 2 PP 119–128.*

Computer Embase Abstract 1998162010 Ebina et al "Antimetastatic Effect of Hot Water Extract of Taheebo" Biotherapy (1998) 12/4 (495–500).*

Edward H. Oswald :"Lapacho", British Journal of Phytotherapy, vol. 3, No. 3, 1993/94, pp. 112–117.

M. Pinkas et al.: "Phenolic components from some species of Grindelia", Annales Pharmaceutiques francais, 1978, vol. 36, No. 3–4, pp. 97–104.

Mariapina Natoli et al.: "Regioselective Alcoholysis of Flavonoid Acetates with Lipase in an Organic Solvent", J. Org. Chem., 1992, vol. 57, pp. 5776–5778.

Lilian E. Pelzer et al.: "Acute and chronic anti–inflammatory effects of plant flovonoids", Chemical Abstracts 129: 310397m, XP–002130345.

M. Masood et al.: "A novel spray reagent for flavones and quinines", Chemical Abstracts 95: 125629b XP–002130341.

Ying Wang et al.: "Antimicrobial flavonoids from Paladia trinervia and their method and acetylated derivatives", Chemical Abstracts 112: 33345a, XP–002130342.

Ludwik Meresta et al.: "Antibacterial activity of flavonoid compounds of propolis", Chemical Abstracts 109: 35198s, XP–002130343.

James T. MacGregor et al.: "Mutagenicity of plant flavonoids: structural requirements for mutagenic activity in Salmonella typhimurium", Chemical Abstracts 90: 81816d, XP–002130344.

* cited by examiner

*Primary Examiner*—Herbert J. Lilling
(74) *Attorney, Agent, or Firm*—Laurence A. Greenberg; Werner H. Stemer; Gregory L. Mayback

(57) ABSTRACT

Products for body hygiene containing Lapacho extracts and also quercitine and possibly other quinones present in Lapacho extracts salified or whatever modified in order to make them soluble in water are described. The preparation of the above said compounds and their use is also described.

13 Claims, No Drawings

PRODUCTS FOR BODY HYGIENE BASED ON LAPACHO EXTRACTS CONTAINING QUERCITINE, THEIR PREPARATION AND USE

SCOPE OF INVENTION

The present invention refers to products for the body hygiene consisting basically of Lapacho extracts and containing, possibly in combination with other excipients and/or active principles, quercitine, and possibly other Lapacho quinones, salified or whatever modified in order to make them soluble in water. The invention refers also to the preparation of such compounds and their use for body hygiene.

STATE OF THE ART

The name Lapacho refers to plants of the genus Tabebubia, family Bignoniacee, whose various species are widely diffused in South America countries.

Since more than one thousand years the plant is used for medical purposes by indigenous populations which use in particular the internal part of the bark obtaining extracts useful in the treatment of various diseases.

Many studies have been performed in order to identify the pharmacological potential of the Lapacho extracts and various active principle have been isolated. Essentially 18 different quinones have been identified (see Edward H. Oswald—British Journal of Phytotherapy, Vol. 3, n. 3 (1993/1994).

The pharmacological properties of various extracts have been studied and it was proved that they possess antibiotic, antiviral, antimicotic, and antiseptic activity which made them appropriated i.a. in the treatment of mouth, nose and throat infections.

It was also observed that the different active principles, once isolated from the other present in the extract, showed a lower therapeutic activity in respect to the total plant extract where by "total plant extract" the solution obtained by the extraction of the bark with hot water according to known techniques is meant.

In particular among the various quinones mentioned above the quercitine is a product of formula (A)

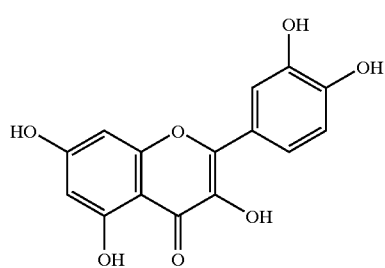

(A)

described in literature as endowed of activity against capillary fragility.

It is important to notice that this compound, due to its hydrophobic nature, is not dissolved in hot water during the extraction process and therefore is not present in the extracts obtained by such technique described in literature and commonly used for the traditional preparations as illustrated above.

DETAILED DESCRIPTION OF INVENTION

It was now surprisingly found that the addition of quercitine, and possibly other quinones, salified or otherwise modified in order to make them soluble in water, to the solution obtained by extracting the bark of Lapacho plants with hot water according to the known techniques, unexpectedly improves the antiseptic properties of the solution making it particularly suitable as product for body hygiene and in particular as collutories.

More particularly it was noticed that derivatives of quercitine of formula (I)

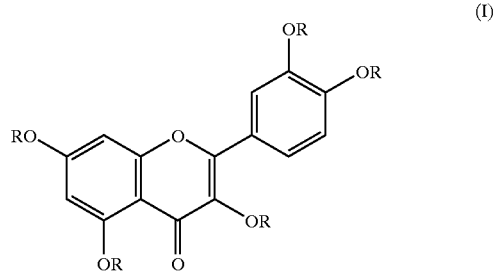

(I)

wherein three or four of the substituents R are H and the remaining one or two, identical, represent a moiety chosen in the group consisting of: Na, K, $C_{1-3}$acyl, benzoyl, $C_{1-3}$alkyl have a particularly marked effect in increasing the antiseptic properties of the extract. All these derivatives are water soluble.

The present invention refers to compounds for body hygiene consisting of an extract of Lapacho bark with hot water, obtained according to the known techniques, comprising also quercitine or its derivatives of formula (I) and possibly other quinones salified in order to make them soluble in hot water.

The above said addition of quinones, normally lacking in the Lapacho extracts in hot water, allows to take advantage of the pharmaceutical properties also of those products which are normally lost in the extracts known up to now and to obtain formulations having unexpected high antiseptic properties.

The invention refers also to the compounds of formula (I) as above defined.

Among the above defined compounds of formula (I) particularly preferred are those wherein the two substituents R, identical between each other and different from H, are an acetyl-group.

The compound for body hygiene according to the invention can obviously contain other excipients and/or active principles for example fluorine salts, zinc oxide, vitamins or other compounds normally used as anti-inflammatory and antiseptic products.

Among the compounds useful for preparing a formulation for the personal hygiene according to the invention (i.e. in combination with the Lapacho extract and quercitine as said above) we can remember: agrimony (*Agrimonia Eupatoria*) extract, althea (*Althaea Officinalis*) extract, *Erysimum Officinalis* extract, cajeputol (*Eucaliptus Globulus*) extract, lemon (*Citrus Limonum*) extract, mallow (*Malvae Officinalis*) extract, *Plantago Officinalis* extract, *Hypericum perforatum* extract, dewaxed propolis, thymus, α-bisabolole, the common natural disinfectants.

To the solution of active principles as above described the excipients normally used in the galenic and/or cosmetic field for the preparation of formulations as for example: collutory, toothpaste, tablet, chewing-gum, ovule or douche, gel, cream, ointment, shampoo and soap can be added according to the desired final product.

A particular example of a product for the personal hygiene according to the present invention has the following composition:

0.5–15% Lapacho extract 0.4–1.5% quercitine and possibly other quinones

1–6% agrimony extract;

1.5–8% althea extract 0.5–8% *Erysimum Officinalis* extract 0.5–6.5% cajeputol extract 0.5–6.5% lemon extract 0.5–6.5% mallow extract 0.5–6% *Plantago Officinalis* extract 0.5–5% propolis (deprived of wax)

conservatives, sweetens and water up to 100.

The above reported percentages are expressed as volume on the total preparation volume.

The compounds for body hygiene according to the present invention can be easily prepared by extracting with hot water according to well known techniques the Lapacho bark and filtering the obtained suspension.

The residue (containing quercitine and possibly other quinones) is dried and the quinones are salified with the appropriated reagents (according to the wanted final product) in order to make them soluble in water thereafter they are added to the solution and the possible suspended residues (consisting of not salified products) is filtered away.

For example, in order to obtain monoacetylated derivatives of quercitine and possible other quinones, the residue remaining after the extraction can be treated with anhydrous acetic acid in the presence of about 1 mole of acetic anhydride and warmed at about 50° C. The so treated residue is suspended in water, filtered and washed with water; thereafter suspended in water wherein a base was added (for example NaOH or KOH up to the formation of a clear solution (if a residue is still present this is eliminated by filtration).

With the above said procedure the quercitine, and possibly other wanted quinones, which remained in the residue after the extraction are solved. The so obtained solution is added to the traditional solution previously obtained by extraction of Lapacho with hot water.

It is evident that instead of treating as above described the natural product remaining after the extraction in hot water, it is possible to directly salify commercially available quercitine by operating as above described. The obtained soluble salt can then be added to the Lapacho extract in hot water in a quantity of 0.4–1.5% calculated on the final product. In this case the final product will obviously lack the salified forms of possibly insoluble quinones different from quercitine which are present in the natural Lapacho.

The obtained product is worked according to the known techniques in order to give a final product in the wanted form as requested for its final use.

The invention will be better understood in the light of the given examples.

Example 1

Preparation of the Lapacho Extract and Salification of Quercitine and Possibly Other Quinones Remained in the Extraction Residue 100 g of Lapacho powder are suspended under stirring in 300 cc of water at 40°–50° C.; the obtained brownish suspension is filtered and the solution is stocked.

The residue is washed with 10 cc of hot water and dried (about 600 mg). The residue is solved in 20 ml glacial acetic acid wherein 1.3 moles of acetic anhydride are added. The reaction is exothermic, once the temperature has lowered to room temperature the solution is kept under stirring for about 12 hours. The precipitate (consisting of diacetyl-derivatives of quercitine and possibly other quinones) is added with 100 cc cold water, filtered, washed and resuspended in 30 ml water. The suspension is treated with NaOH 10% up to formation of a clear solution. The remaining solid is eliminated by filtration and the filtered solution is added to the previously stocked solution.

Preparation of a Collutory 30 g. of Lapacho extract and 6 g. of monoacetylated quercitine are mixed together in a mixer in combination with 30 g. agrimony extract, 50 g. althea extract, 50 g. *Erysimum Officinalis* extract, 30 g. cajeputol extract, 30 g. lemon extract, 30 g. mallow extract, 30 g. *Plantago Officinalis*, 15 g. dewaxed propolis, conservatives sweetens and water up to 1000 g.

Using analogous quantities of active principles (i.e. Lapacho extracts and acetylated quercitine) and the appropriated excipients the different formulations for body hygiene as above mentioned are obtained according to the corresponding known techniques.

What is claimed is:

1. A product for body hygiene made according to a method which comprises:

providing Lapacho bark containing soluble and insoluble quinones;

extracting the quinones from the Lapacho bark with water to create a first solution of the soluble quinones, the first solution suspending the insoluble quinones;

filtering the first solution to separate the insoluble quinones from the first solution;

drying the insoluble quinones;

salifying some of the insoluble quinones to yield salified quinones and unsalified quinones;

dissolving the salified quinones in water to create a second solution, the unsalified quinones being suspended in the second solution;

separating the unsalified quinones from the second solution; and combining the first solution and the second solution.

2. A toothpaste, comprising a product for body hygiene according to claim 1.

3. A callutory, comprising a product for body hygiene according to claim 1.

4. A tablet, comprising a product for body hygiene according to claim 1.

5. A chewing-gum, comprising a product for body hygiene according to claim 1.

6. A douche, comprising a product for body hygiene according to claim 1.

7. A gel, comprising a product for body hygiene according to claim 1.

8. A cream, comprising a product for body hygiene according to claim 1.

9. The product according to claim 1, wherein the salifying step produces a monoacetyl derivate of the insoluble quinone.

10. A shampoo, comprising a product for body hygiene according to claim 1.

11. A soap, comprising a product for body hygiene according to claim 1.

12. A method for producing a product for body hygiene, which comprises:

providing Lapacho bark containing soluble and insoluble quinones;

extracting the quinones from the Lapacho bark with water to create a first solution of the soluble quinones, the first solution suspending the insoluble quinones;

filtering the first solution to separate the insoluble quinones from the first solution;

drying the insoluble quinones;

salifying some of the insoluble quinones to yield salified quinones and unsalified quinones;

dissolving the salified quinones in water to create a second solution, the unsalified quinones being suspended in the second solution;

separating the unsalified quinones from the second solution; and combining the first solution and the second solution.

13. The method according to claim 12, wherein the salifying step includes:

adding, to the insoluble quinones, anhydrous acetic acid and acetic anhydride in water to form a third solution, heating the third solution to 50° C., a residue of the insoluble quinones not dissolving in the third solution, suspending the residue in water, filtering the residue to separate the reside from the third solution, filter washing the residue with water, suspending the residue in a basic aqueous solution, removing the residue, and adding the basic aqueous solution to the first and second solutions.

* * * * *